United States Patent
Wang et al.

(10) Patent No.: US 6,534,267 B1
(45) Date of Patent: Mar. 18, 2003

(54) POLYNUCLEOTIDES ENCODING ACTIVATORS OF CASPASES

(76) Inventors: Xiaodong Wang, Dept. Biochemistry, UTSW Medical Center, 5323 Harry Hines Blvd., Dallas, TX (US) 75235-9038; Chunying Du, Dept. Biochemistry, UTSW Medical Center, 5323 Harry Hines Blvd., Dallas, TX (US) 75235-9050

( * ) Notice: Subject to any disclaimer, the term of this patent is extended or adjusted under 35 U.S.C. 154(b) by 298 days.

(21) Appl. No.: 09/627,393

(22) Filed: Jul. 28, 2000

Related U.S. Application Data

(63) Continuation of application No. 09/479,309, filed on Jan. 6, 2000, now Pat. No. 6,110,691.

(51) Int. Cl.$^7$ ................................................. C12Q 1/68
(52) U.S. Cl. .......................... 435/6; 536/23.1; 536/23.2; 536/23.5
(58) Field of Search ............................... 536/23.1, 23.2; 435/23.5, 6

(56) References Cited

PUBLICATIONS

GenBank Accession No. 150224.
GenBank Accession No. CAA84332.
GenBank Accession No. AW161050 (Nov. 9, 1999).*
GenBank Accession No. AA303823 (Apr. 18, 1997).*
GenBank Accession No. AI906387 (Dec. 1, 1999).*
GenBank Accession No. AA325771 (Apr. 20, 1997).*
GenBank Accession No. AA129950 (Nov. 27, 1997).*
GenBank Accession No. AI339459 (Dec. 29, 1998).*

* cited by examiner

*Primary Examiner*—Ponnathapu Achutamurthy
*Assistant Examiner*—Kathleen Kerr
(74) *Attorney, Agent, or Firm*—Richard Aron Osman

(57) ABSTRACT

The invention provides methods and compositions relating to human polypeptide activators of caspases such as polypeptide and polynucleotide sequences diagnostic of caspase activators. These sequences and polypeptides and polynucleotides embodying these sequences find a wide variety of diagnostic and therapeutic applications involving detecting and/or modulating expression and/or function of activators or caspases or genes or transcripts encoding such activators and generating genetic and immuno probes specific to activators of caspases.

15 Claims, No Drawings

POLYNUCLEOTIDES ENCODING ACTIVATORS OF CASPASES

CROSS-REFERENCE TO RELATED APPLICATION

This application claims priority under 35 U.S.C. §120 and is a continuation to Ser. No. 09/479,309, filed Jan. 6, 2000, now U.S. Pat. No. 6,110,691 which is incorporated herein by reference.

The research carried out in the subject application was supported in part by grants from the National Institutes of Health (GMRO1-57158). The government may have rights in this invention.

FIELD OF THE INVENTION

The field of the invention is regulators of enzymes involved in cellular apoptosis.

BACKGROUND

One of the key regulatory steps for apoptosis is the activation of caspases, leading to the characteristic morphological changes associated with apoptotic cells including chromatin condensation, DNA fragmentation into nucleosomal fragments, nuclear membrane break down, externalization of phosphotidylserine and formation of apoptotic bodies that are readily phagocytosed (Liu et al., 1997 Cell 89, 175–184; Enari et al., 1998 Nature 391, 43–50; Sahara, et al., 1999 Nature 401, 168–173; Lazebnik, et al., 1995 Proc. Natl. Acad. Sci. USA 92, 9042–9046; Martin et al., 1996 J. Biol. Chem. 271, 28753–28756; Zhang et al., 1999 J. Cell Biol. 145, 99–108).

One major apoptotic caspase activation cascade is triggered by cytochrome c, a protein that normally functions in the electron transfer chain in mitochondria (Liu et al., 1996 Cell 86, 147–157). In living cells, holocytochrome c exists exclusively in the intermembrane space of mitochondria, and is therefore sequestered away from its deadly cytosolic partner, Apaf-1 (Zou et al., 1997 Cell 90, 405–413). Upon receiving apoptotic stimuli, such as serum deprivation, activation of cell surface death receptors, and excessive damage of DNA, the outer membrane of mitochondria becomes permeable to cytochrome c (Reviewed by Reed, 1997 Cell 91, 559–562). Once released to cytosol, cytochrome c binds to Apaf-1 with 2:1 stoichiometry and forms an oligomeric Apaf-1/cytochrome c complex in the presence of dATP or ATP (Purring et al., 1999 J. American Chem. Soc. 121, 7435–7436; Zou et al., 1999 J. Biol. Chem. 274, 11549–11556). This oligomerized Apaf-1/cytochrome c complex then recruits and activates the apical caspase of this pathway, procaspase-9 (Li et al., 1997 Cell 91, 479–489; Zou et al., 1999). Caspase-9 in turn activates downstream caspases such as caspase-3, -6 and -7 that constitute the major caspase activity in an apoptotic cell (Li et al., 1997; Srinivasa et al., 1998 Mol. Cell 1, 949–957; Faleiro et al., 1997 EMBO J; 16, 2271–2281).

Here we disclose the identification, purification, molecular cloning, and characterization of a novel factor that promotes cytochrome c/Apaf-1-dependent caspase activation. Like cytochrome c, this protein is normally located in mitochondria and released into cytosol when cells undergo apoptosis. We named this protein Smac, for the second mitochondria-derived activator of caspase, after cytochrome c. Addition of Smac to cytosolic extracts causes robust caspase activation in these extracts even without the addition of dATP. Smac also allows caspase activation in the presence of physiological levels of potassium salt.

SUMMARY OF THE INVENTION

The invention provides methods and compositions relating to polypeptide regulators (activators and inhibitors) of enzymes involved in cellular apoptosis, particularly caspases In a particular aspect, the invention provides polypeptide and polynucleotide sequences diagnostic of caspase activators. These sequences and polypeptides and polynucleotides embodying these sequences find a wide variety of diagnostic and therapeutic applications involving detecting and/or modulating expression and/or function of activators or caspases or genes or transcripts encoding such activators. In more particular aspects, the invention provides genetic and immuno probes specific to activators of caspases.

Since undesirable activation or inactivation of apoptosis has been associated with many human diseases such as cancer, autoimmune disease and neurodegenerative diseases, the disclosed caspase regulatory polypeptides and polynucleotides provide both drug targets and regulators to promote or inhibit apoptosis. Also, since disclosed native Smac proteins naturally translocate from mitochondria to cytosol during apoptosis, Smac proteins can be used as diagnostic markers for apoptosis during normal or disease stages, e.g. using labeled Smac proteins such as fusion proteins or using detectable Smac-specific binding agents.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The subject polypeptide sequences find a wide variety of applications. In one embodiment, the subject sequences are used to synthesize polypeptides which in turn provide a number of applications, including use in proteomic microarrays (e.g. Silzel J W, et al. Clin Chem 1998 September;44 (9):2036–43), models for rationale drug design, immunogens for antibody elicitation, etc. The polypeptide sequences are also used to specifically detect sequences comprising SEQ ID NO:2, or fragments thereof, particularly at least one of SEQ ID NO:2, residues 1–78 or SEQ ID NO:2, residues 176–239, or fragments thereof, or polypeptides comprising such sequences. Any convenient sequence detection method may be used, including computational methods for direct sequence detection (e.g. BLAST-type algorithms, alignments, etc.) and physical methods for inferential sequence detection of polymers (e.g. mass spectroscopy, etc.).

In addition to direct synthesis, the subject polypeptides can also be expressed in cell and cell-free systems (e.g. Jermutus L, et al., Curr Opin Biotechnol. 1998 October;9 (5):534–48) from encoding polynucleotides, such as the corresponding parent polynucleotides or naturally-encoding polynucleotides isolated with degenerate oligonucleotide primers and probes generated from the subject polypeptide sequences ("GCG" software, Genetics Computer Group, Inc, Madison Wis.) or polynucleotides optimized for selected expression systems made by back-translating the subject polypeptides according to computer algorithms (e.g. Holler et al. (1993) Gene 136, 323–328; Martin et al. (1995) Gene 154, 150–166).

The subject polypeptides include fragments of the recited sequences which have Smac-specific amino acid sequence, binding specificity or function. Preferred fragments comprise at least 8, preferably at least 10, preferably at least 15, more preferably at least 25, more preferably at least 35, most preferably at least 50 consecutive residues of SEQ ID NO:2, particularly of at least one of SEQ ID NO:2, residues 1–78 or SEQ ID NO:2, residues 176–239, and have corresponding-polypeptide-specific antibody binding, elicitation or binding or elicitation inhibitory activity.

Specific activity or function may be determined by convenient in vitro, cell-based, or in vivo assays: e.g. in vitro binding assays, etc. Binding assays encompass any assay where the molecular interaction of a subject polypeptide with a binding target is evaluated. The binding target may be a natural binding target such as a regulating protein or a non-natural binding target such as a specific immune protein such as an antibody, or a specific agent such as those identified in screening assays such as described below. Binding specificity may be assayed by binding equilibrium constants (usually at least about $10^7$ $M^{-1}$, preferably at least about $10^8$ $M^{-1}$, more preferably at least about $10^9$ $M^{-1}$), by caspase activation or apoptosis assays, by the ability of the subject polypeptide to function as negative mutants in expressing cells, to elicit specific antibody in a heterologous host (e.g a rodent or rabbit), etc. In a particular embodiment, the subject polypeptide fragments provide specific antigens and/or immunogens, especially when coupled to carrier proteins. For example, peptides are covalently coupled to keyhole limpet antigen (KLH) and the conjugate is emulsified in Freunds complete adjuvant. Laboratory rabbits are immunized according to conventional protocol and bled. The presence of specific antibodies is assayed by solid phase immunosorbant assays using immobilized corresponding polypeptide, see, e.g. Table 1.

TABLE 1

Immunogenic Smac polypeptides eliciting specific rabbit polyclonal antibody: Polypeptide-KLH conjugates immunized per protocol described above.

| Polypeptide Sequence | Immunogenicity |
| --- | --- |
| SEQ ID NO: 2, residues 1–8 | +++ |
| SEQ ID NO: 2, residues 4–13 | +++ |
| SEQ ID NO: 2, residues 7–17 | +++ |
| SEQ ID NO: 2, residues 13–24 | +++ |
| SEQ ID NO: 2, residues 18–27 | +++ |
| SEQ ID NO: 2, residues 35–49 | +++ |
| SEQ ID NO: 2, residues 47–54 | +++ |
| SEQ ID NO: 2, residues 71–78 | +++ |
| SEQ ID NO: 2, residues 83–92 | +++ |
| SEQ ID NO: 2, residues 115–124 | +++ |
| SEQ ID NO: 2, residues 141–148 | +++ |
| SEQ ID NO: 2, residues 166–174 | +++ |
| SEQ ID NO: 2, residues 176–184 | +++ |
| SEQ ID NO: 2, residues 183–191 | +++ |
| SEQ ID NO: 2, residues 192–200 | +++ |
| SEQ ID NO: 2, residues 201–208 | +++ |
| SEQ ID NO: 2, residues 209–216 | +++ |
| SEQ ID NO: 2, residues 215–222 | +++ |
| SEQ ID NO: 2, residues 223–231 | +++ |
| SEQ ID NO: 2, residues 232–239 | +++ |

The subject polypeptides and fragments thereof are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The polypeptides may be synthesized, produced by recombinant technology, or purified from cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to the subject polypeptides, methods of identifying and making such agents, and their use. For example, specific binding agents are useful in a variety of diagnostic and industrial applications and include somatically recombined polypeptide receptors like specific antibodies or T-cell antigen receptors (see, e.g. Harlow and Lane (1988) Antibodies, A Laboratory Manual, Cold Spring Harbor Laboratory), intracellular binding agents identified with assays such as one-, two- and three-hybrid screens, non-natural intracellular binding agents identified in screens of chemical libraries such as described below, etc. Accordingly, the invention provides complementarity determining region (CDR) sequences and libraries of such sequences.

The subject CDR sequences find a wide variety of applications. In one embodiment, the subject CDR sequences are used to synthesize polypeptides which in turn provide a number of applications, including immuno-microarrays, affinity reagents, etc. In addition to direct synthesis, the subject CDR polypeptides can also be expressed in cell and cell-free systems (e.g. Jermutus L, et al., Curr Opin Biotechnol. 1998 October;9(5):534–48) from encoding polynucleotides, such as the corresponding parent polynucleotides or naturally-encoding polynucleotides isolated with degenerate oligonucleotide primers and probes generated from the subject polypeptide sequences ("GCG" software, Genetics Computer Group, Inc, Madison Wis.) or polynucleotides optimized for selected expression systems made by back-translating the subject polypeptides according to computer algorithms (e.g. Holler et al. (1993) Gene 136, 323–328; Martin et al. (1995) Gene 154, 150–166). Generally, the CDR polypeptides are expressed and used as the binding domain of an immunoglobulin or fragment thereof.

The invention provides efficient methods of identifying agents, compounds or lead compounds for agents which modulate the ability of the subject polypeptides to interact with a binding target. A wide variety of assays for binding agents are provided including labeled in vitro protein-protein binding assays, immunoassays, caspase activation assay, cell-based assays such as apoptosis assays, etc. The methods are amenable to automated, cost-effective high throughput screening of chemical libraries for lead compounds. In vitro binding assays employ a mixture of components including the subject polypeptide, which may be part of a fusion product with another peptide or polypeptide, e.g. a tag for detection or anchoring, etc. The assay mixtures comprise a binding target. In a particular embodiment, the binding target is an antibody specific for the polypeptide. While native full-length binding targets may be used, it is frequently preferred to use portions thereof so long as the portion provides binding affinity and avidity to the subject polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like, salts, buffers, neutral proteins, e.g. albumin, detergents, protease inhibitors, nuclease inhibitors, antimicrobial agents, etc. may be used. The resultant mixture is incubated under conditions whereby, but for the presence of the candidate pharmacological agent, the polypeptide specifically binds the binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening. After incubation, the agent-biased binding between the polypeptide and one or more binding targets is detected by any convenient way. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the polypeptide to the target in the absence of the agent as compared with the binding affinity in the presence of the agent indicates that the agent modulates the binding of the polypeptide to the binding target. A difference, as used herein, is statistically significant and preferably represents at least a 50%, more preferably at least a 90% difference.

The subject polynucleotide sequences find a wide variety of applications. For example, the polynucleotide sequences are also used to specifically detect Smac sequences, particularly SEQ ID NO:1, its reverse complement or a fragment thereof, preferably at least one of SEQ ID NO:1, nucleotides 1–234 or SEQ ID NO:1, nucleotides 525–720, a reverse complement of either, or a fragment of any thereof, or polynucleotides comprising such sequences. Any convenient sequence detection method may be used. In one embodiment, candidate or unknown sequences are determined and compared with a disclosed sequence to classify the candidate or unknown sequences. For example, an algorithm such as BLAST (e.g. Build sol2.5-x86 01:40:37 Feb. 5, 1998, Copyright (C)1997 Warren R. Gish, using default parameters, Altschul et al., Methods in Enzymology, 215: 403–410 (1997)) may be used to define relatedness to one or more subject sequence diagnostic of Smac-relatedness in computer-based methods.

In another embodiment, the disclosed sequences are used to synthesize and/or are embodied in polynucleotides which in turn provide a number of applications, including microarray-based methodologies, see e.g. Nat Genet 1999 January;21(1 Suppl), entire issue incl. Debouck C, et al. at 48–50; gene expression analysis, see e.g. Carulli J P, et al., J Cell Biochem Suppl 1998;30–31:286–96; drug target discovery and design, see, e.g. Jones D A, et al., Curr Opin Chem Biol 1999 February;3(1):71–6; combinatorial chemistry, see, e.g. Lukas T J, et al., J Med Chem. 1999 March 11;42(5):910–919; ribozymes and therapeutics, see e.g. Rossi J J, Chem Biol 1999 February;6(2):R33–7; mapping; etc. In one embodiment, candidate and/or unknown polynucleotides may be isolated, compared and/or classified (e.g. by relatedness) by hybridization to one or more disclosed polynucleotide, e.g using microarrayed libraries of disclosed polynucleotides. Such polynucleotides may also be used as probes and/or primers to localize, isolate, amplify, etc., natural genes and transcripts. In another embodiment, the disclosed polynucleotides or fragments or libraries of such polynucleotides are transfected into cells for a wide variety of cloning, display, expression, etc. applications, including 'n'-hybrid systems, see, e.g. Vidal M, et al., 1999, Nucleic Acids Res. 27(4):919–929 & Proc Natl Acad Sci U S A. 93(19):10315–20 & 10321–6; mapping protein-ligand interactions using whole genome phage display libraries, see e.g. Palzkill T, et al., Gene 1998 October 9;221(1):79–83; DNA-based selection and screening of peptide ligands, see e.g. Bartoli F, et al., Nat Biotechnol 1998 November;16(11): 1068–73, etc.

In a particular embodiment, the invention provides microarrays of the disclosed polynucleotides and their uses as described or cited herein. A wide variety of materials and methods are known in the art for arraying polynucleotides at discrete elements of substrates such as glass, silicon, plastics, nylon membranes, etc., including contact deposition, e.g. U.S. Pat. Nos. 5,807,522; 5,770,151, DeRisi J L, et al. Curr Opin Oncol 1999 January;11(1):76–9, etc.; photolithography-based methods, e.g. U.S. Pat Nos. 5,861, 242; 5,858,659; 5,856,174; 5,856,101; 5,837,832, Lipshutz R J, et al. Nat Genet 1999 January;21(1 Suppl):20–4, etc.; inkjet dispensing technologies, e.g. Lemmo A V, et al., Curr Opin Biotechnol 1998 December;9(6):615–7; flow path-based methods, e.g. U.S. Pat. No. 5,384,261; dip-pen nanolithography-based methods, e.g. Piner, et al., Science Jan. 29, 1999: 661–663, etc.; etc.

The invention also provides polynucleotides which hybridize to a polynucleotide having a sequence of SEQ ID NO:1, or to its reverse complement. In a particular embodiment, the invention encompasses a recombinant first polynucleotide comprising a sequence at least 36, preferably at least 48, more preferably at least 96 nucleotides in length, the sequence having sequence similarity with a second polynucleotide consisting of SEQ ID NO:1, preferably SEQ ID NO:1, nucleotides 1–234 or SEQ ID NO:1, nucleotides 525–720, or a reverse complement thereof, such that the sequence and second polynucleotide specifically hybridize under a hybridization condition under hybridization condition #1, preferably #2, more preferably #3 and so on to #10, as identified and described in Tables A–C. Thus, for example, if hybridization condition #7 is preferred, then the conditions used for identifying and classifying related or homologous polynucleotides employ hybridization buffer M at a hybridization temperature of 40° C., and wash buffer E at a wash temperature of 55° C. Condition #1 identifies polynucleotides having at least about 50% sequence identity with the target polynucleotide (with % identity calculated as described herein). With each subsequent condition, the stringency is such that the isolated polynucleotide has a sequence identity of at least 5% greater than what would be isolated by using the next lower condition number. Thus, for example, condition #2 identifies polynucleotides having at least about 55% sequence identity with the target polynucleotide, and conditions #9 and #10 identify polynucleotides having at least about 90% and 95% sequence identity, respectively, to the target polynucleotide.

SEQ ID NO:1 is derived from a natural human transcript encoding a natural Smac (see Examples, below). Exemplary higher stringency hybridizing polynucleotides of SEQ ID NO1 (having SEQ ID NO:1 sequence identities of about 95%) are designated SEQ ID NOS:3–5 and exemplary lower stringency hybridizing polynucleotides of SEQ ID NO:1 (having SEQ ID NO:1) sequence identities of about 90%) are designated SEQ ID NOS:6–8 in the Sequence Listing. In situations where it is desired to classify more closely related polynucleotides, the hybridization condition is increased by increments of one, until the desired specificity is obtained. Preferably, each hybridizing polynucleotide has a length that is at least 30%, preferably at least 50%, more preferably at least 70% and most preferably at least 90% of the length of the polynucleotide sequence described herein to which it hybridizes.

In Tables A and B, formamide is expressed as percent (v/v) in a buffered diluent comprising 1× to 6×SSC (1×SSC is 150 mM NaCl and 15 mM sodium citrate; SSPE may be substituted for SSC, 1×SSPE is 150 mM NaCl, 10 mM Na H$_2$PO$_4$, and 1.25 mM EDTA, pH7.4). Procedures for polynucleotide hybridizations are well-known in the art (see Ausubel et al., *Current Protocols in Molecular Biology*, Wiley Interscience Publishers, (1995); Sambrook et al., *Molecular Cloning: A Laboratory Manual*, New York: Cold Spring Harbor Press, 1989; Shilo and Weinberg, 1981, *Proc. Natl. Acad. Sci.* U.S.A. 78, 6789–6792; and PCT publication WO 99/01466).

TABLE A

| Hybridization Buffer | X SSC | % Formamide |
|---|---|---|
| G | 1 | 25 |
| H | 2 | 25 |
| I | 3 | 25 |
| J | 4 | 25 |
| K | 5 | 25 |
| L | 6 | 25 |
| M | 1 | 0 |
| N | 2 | 0 |
| O | 3 | 0 |
| P | 4 | 0 |
| Q | 5 | 0 |
| R | 6 | 0 |

TABLE B

| Wash Buffer | X SSC |
|---|---|
| A | 0.2 |
| B | 0.3 |
| C | 0.4 |
| D | 0.5 |
| F | 0.6 |
| F | 0.8 |
| G | 1 |
| H | 2 |
| I | 3 |
| L | 4 |
| K | 5 |
| L | 6 |

TABLE C

| Hybridization Condition # | Hybridization Buffer | Hybridization Temperature | Wash Buffer | Wash Temperature |
|---|---|---|---|---|
| 1 | R | 25° C. | L | 35° C. |
| 2 | R | 25° C. | L | 40° C. |
| 3 | R | 27° C. | L | 47° C. |
| 4 | R | 34° C. | M | 45° C. |
| 5 | R | 40° C. | F | 45° C. |
| 6 | O | 40° C. | E | 50° C. |
| 7 | M | 40° C. | E | 55° C. |
| 8 | L | 42° C. | D | 60° C. |
| 9 | M | 42° C. | C | 65° C. |
| 10 | Q | 42° C. | B | 70° C. |

The invention also provides fragments of the parent and/or homolog polynucleotides which may be used in the foregoing methods, especially as nucleic acid hybridization probes and replication/amplification primers. These fragments are of length sufficient to specifically the corresponding SEQ ID NO or complement thereof, generally comprising at least 12, preferably at least 24, more preferably at least 36 and most preferably at least 96 contiguous nucleotides of the corresponding SEQ ID NO (see, e.g. Table 2).

TABLE 2

Exemplary Smac polynucleotide fragments which hybridize with a strand of SEQ ID NO: 1 under hybridization condition #5.

| Polynucleotide fragment | Hybridization |
|---|---|
| SEQ ID NO: 1, nucleotides 1–24 | + |
| SEQ ID NO: 1, nucleotides 18–42 | + |
| SEQ ID NO: 1, nucleotides 45–69 | + |
| SEQ ID NO: 1, nucleotides 75–92 | + |
| SEQ ID NO: 1, nucleotides 116–141 | + |
| SEQ ID NO: 1, nucleotides 166–199 | + |
| SEQ ID NO: 1, nucleotides 211–234 | + |
| SEQ ID NO: 1, nucleotides 255–299 | + |
| SEQ ID NO: 1, nucleotides 359–383 | + |
| SEQ ID NO: 1, nucleotides 436–460 | + |
| SEQ ID NO: 1, nucleotides 491–513 | + |
| SEQ ID NO: 1, nucleotides 525–548 | + |
| SEQ ID NO: 1, nucleotides 575–598 | + |
| SEQ ID NO: 1, nucleotides 624–648 | + |
| SEQ ID NO: 1, nucleotides 644–669 | + |
| SEQ ID NO: 1, nucleotides 649–672 | + |
| SEQ ID NO: 1, nucleotides 654–677 | + |
| SEQ ID NO: 1, nucleotides 665–688 | + |
| SEQ ID NO: 1, nucleotides 687–710 | + |
| SEQ ID NO: 1, nucleotides 697–720 | + |

The subject polynucleotides include fragments of the recited sequences which have Smac-specific sequence. Preferred fragments comprise at least 34, preferably at least 36, preferably at least 56, more preferably at least 96, more preferably at least 186 consecutive nucleotides of SEQ ID NO:1, particularly of at least one of SEQ ID NO:1, nucleotides 1–234 or SEQ ID NO:1, nucleotides 525–720, a reverse complement of either. The subject polynucleotides and fragments thereof may be joined to other components such as labels or other polynucleotide/polypeptide sequences (i.e. they may be part of larger sequences) and are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant polynucleotides comprising the subject SEQ ID NOs, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bases, most preferably fewer than 100 bases, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

EXAMPLES

I. DNA Microarray Construction and Use for Smac Expression Measurements

Comparative gene expression using microarrayed polynucleotide libraries is performed substantially as described by DeRisi, et al. Science 1997 October 24; 278: 680–686. Microarrayer design and construction are performed as published Aug. 10, 1998 by Brown et al., Stanford University Department of Biochemistry, at http://cmgm.stanford.edu/pbrown/mguide/index.html. All procedures are done at room temperature and with double distilled water unless otherwise stated. Software: J. DeRisi and V. Iyer (1999) Array Maker v1.5, published Feb. 15, 1999 at http://cmgm.stanford.edu/pbrown/mguide/software.html.

| 1. Preparation of Slides | | | |
|---|---|---|---|
| Materials | Qty | Order info | |
| Glass microscope slides | 60 | Gold Seal #3010 | |
| Slide rack | 2 | Shandon Lipshaw #121 | <= Each rack holds 30 slides |
| Slide chamber | 6 | Shandon Lipshaw #121 | <= Each chamber holds 350 mL |
| ddH2O | ~5 L | | |
| NaOH | 70 g | | |
| 95% Ethanol | 420 mL | | |
| Poly-L-lysine | 70 mL | Sigma #P 8920 | |
| Tissue culture PBS | 70 mL | | |
| Vacuum oven (45 C.) | | | |
| Slide box | 1 | Research Products International #163000 | |

1. Place slides in slide racks. Place racks in chambers.
2. Prepare CLEANING SOLUTION: Dissolve 70 g NaOH in 280 mL ddH2O. Add 420 mL 95% ethanol. Total volume is 700 mL (=2×350 mL); stir until completely mixed. If solution remains cloudy, add ddH2O until clear.
3. Pour solution into chambers with slides; cover chambers with glass lids. Mix on orbital shaker for 2 hr. Once slides are clean, they should be exposed to air as little as possible. Dust particles will interfere with coating and printing.
4. Quickly transfer racks to fresh chambers filled with ddH2O. Rinse vigorously by plunging racks up and down. Repeat rinses 4× with ddH2O. It is critical to remove all traces of NaOH-ethanol.
5. Prepare POLYLYSINE SOLUTION: 70 mL poly-L-lysine+70 mL tissue culture PBS in 560 mL water. Use plastic graduated cylinder and beaker.
6. Transfer slides to polylysine solution and shake 15 min.–1 hr.
7. Transfer rack to fresh chambers filled with ddH2O. Plunge up and down 5× to rinse.
8. Centrifuge slides on microtiter plate carriers (place paper towels below rack to absorb liquid) for 5 min. @ 500 rpm. Transfer slide racks to empty chambers with covers for transport to vacuum oven.
9. Dry slide racks in 45 C. vacuum oven for 10 min. (Vacuum is optional.)
10. Store slides in closed slide box.
11. BEFORE PRINTING ARRAYS: Check a sample slide to make sure it's hydrophobic—a drop of water should bead off it. Check that polylysine coating is not opaque. Test print, hyb and scan sample slides to determine slide batch quality.

2. Preparation of DNA Samples

Clones of parent polynucleotides are amplified by PCR in 96-well format with amino-linked primers at the 5' end. Purified PCR products are suspended at a concentration of ~0.5 mg/ml in 3×SSC, and ~5 ng of each product arrayed onto coated glass by means of procedures described below. A total of 10,000 elements are arrayed onto an area of 1.8 cm by 1.8 cm with the elements spaced 175 μm apart.

DNA Precipitations

1. Transfer DNA to 96-well V-bottom tissue culture plates (Costar).
2. Add 1/10 vol. 3M sodium acetate (pH 5.2)+equal volume isopropanol. Store at −20 C. for a few hours.
3. Centrifuge in Sorvall at 3500 rpm for 45 min.
4. Rinse with 70% ethanol, centrifuge again.
5. Air dry overnight by covering plates with foil or inverting plates on paper towels. Alternatively, dry plates in a speed-vac (5 min.).
5. Resuspend DNA in 30 uL 3×SSC overnight.
6. Transfer in 4 uL aliquots to 384-well plates (Corning Costar #6557) to make 7 duplicate print plate sets. Tightly seal plates with aluminum foil (R. S. Hughes #425-3) for storage. For long term storage, dry down print plate sets and store at room temp. Before use, resuspend pellets in 4 uL dH2O overnight.
7. Spot DNA onto polylysine slides with 16-tip arrayer. Dry down used print plates for storage between 2nd and 3rd time use.

3. Post-Processing of Arrays

The microarrays are then postprocessed to fix the DNA to the glass surface before hybridization with the procedure described below:

| Materials for 30 arrays | Qty | Order info |
|---|---|---|
| Humid chamber | 1 | Sigma #H 6644 |
| Inverted heat block (70–80° C.) | 1 | |
| Diamond scriber | 1 | VWR #52865-005 |
| Slide rack | 1 | Shandon Lipshaw #121 |
| Slide chamber | 2 | Shandon Lipshaw #121 |
| Succinic anhydride | 5.5 g | Aldrich #23,969-0 |
| 1-Methyl-2-pyrrolidinone | 325 mL | Aldrich #32,863-4 |
| Sodium borate (1 M, pH 8) | 25 mL | <= Use boric acid and adjust pH with NaOH |
| ddH2O | ~1 L | |
| 2L beaker | 1 | |
| 95% ethanol | 350 mL | |

1. REHYDRATE ARRAYS: Fill bottom of humid chamber with 1×SSC. Place arrays face down over 1×SSC and cover chamber with lid. Rehydrate until array spots glisten. Allow spots to swell slightly but not run into each other.
2. Snap-dry each array (DNA side up) on a 70–80 C. inverted heat block for 3 seconds.
3. Mark boundaries of array on back of slide using diamond scriber. Array will become invisible after post-processing.
4. UV crosslink DNA to glass with Stratalinker set for 65 mJ. (Set display to "650", which is 650×100 uJ.) (Optional.)
5. Place arrays in slide rack. Have empty slide chamber ready on orbital shaker.
6. Prepare BLOCKING SOLUTION: Dissolve 5.5 g succinic anhydride in 325 mL 1-methyl-2-pyrrolidinone. Immediately after succinic anhydride dissolves, add 25 mL sodium borate.
7. Immediately after sodium borate solution mixes in, pour solution into empty slide chamber. Plunge slide rack in solution several times. Mix on orbital shaker 15–20 min. Meanwhile, heat ~700 mL water (enough to cover slide rack) to 95 C. in 2 L beaker.

8. Gently plunge slide rack in 95 C. water for 2 min.
9. Plunge slide rack 5× in 95% ethanol.
10. Centrifuge slides on microtiter plate carriers (place paper towels below rack to absorb liquid) for 5 min. @ 500 rpm.
11. Use arrays immediately or store in slide box. Centrifuge 1 min. at top speed.

4. Hybridization of Arrays

All measurements are stored in a computer database for analysis which demonstrate Smac-specific expression.

Directions for fluorescent DNA probes:

1. Final probe volume should be 10–12 uL, at 4×SSC, containing competitor DNA etc. as required
2. Set up array in hybridization chamber. Place 10 uL 3×SSC on edge of slide to provide humidity.
3. Add 0.3 uL 10% SDS to probe.
4. Boil probe for 2 min.
5. Pipet probe onto array, and gently place 22 mm×22 mm cover slip over it.
6. Close hybridization chamber and submerge in 63 C. water bath.
7. Hybridize 4–24 hr.
8. Disassemble hybridization chamber and rinse array in 1×SSC/0.03% SDS.
9. Transfer array to fresh slide rack and rinse 2nd time in 0.2×SSC.
10. Rinse 3rd time in 0.05×SSC. It is critical to remove all SDS.
11. Centrifuge slides on microtiter plate carriers (place paper towels below rack to absorb liquid) for 5 min. @ 500 rpm.
12. Scan array immediately.

II. Identification and Characterization of Natural Smac Polypeptides and Polynucleotides Identification of Smac. In a serendipitous experiment, we noticed that cell extracts prepared in a buffer containing detergents had significantly more caspase-3 activating activity compared with that prepared in the buffer without detergent. Reasoning that there could be a membrane-bound factor that promotes caspase-3 activation in addition to the known water soluble factors Apaf-1, cytochrome c, and procaspase-9, we solublized the membrane pellet in a detergent and added it back to the 100,000×g supernatant of buffer soluble extracts, (S-100). The detergent solublized membrane extracts (SME) did not have caspase-3 activating activity by itself, but significantly stimulated the caspase-3 activating activity when added to the S-100 fraction. Simply adding the same amount of detergent to S-100 had no effect on caspase-3 activation. This experiment indicates that there is a caspase-3 activation promoting factor in the membrane fraction that is normally lacking in the water soluble fraction.

Our previous biochemical fractionation and reconstitution experiments based solely on the S-100 extracts have allowed us to identify three proteins that are necessary and sufficient to reconstitute the caspase-3 activation reaction in the presence of 1 mM dATP. These proteins are Apaf-1, a 130-kDa protein that is the mammalian homologue of CED-4 protein in C. elegans (Zou et al., 1997; Yuan and Horvitz 1992 Development 116, 309–320); procaspase-9 (Li et al., 1997), and cytochrome c that was released into the S-100 during the homogenization procedure (Liu et al, 1996). To examine whether the detergent-solublized membrane extracts contain proteins that substitute Apaf-1, or cytochrome c, or procaspase-9, we first immunodepleted these three proteins individually from the S-100 extracts and added the detergent-solublized membrane fraction to these depleted extracts. No caspase-3 activating activity was observed in these depleted extracts, indicating that this factor cannot substitute Apaf-1, cytochrome c, or procaspase-9. Furthermore, the activity of this factor depends on the presence of Apaf-1, cytochrome c, and procaspase-9. We named this activity Smac for the second mitochondria-derived activator of caspase, because this protein is normally located in mitochondria.

Purification of Smac. Using a reconstitution experiment as an assay, we fractionated the membrane fraction from large cultured HeLa cells solublized in 0.5% CHAPS. The activity of Smac was scored for its ability to stimulate caspase-3 activation in S-100. The purification of Smac was achieved through a six-step procedure (see Experimental Procedures, below). The Smac activity was eluted from the Mono Q column as a single peak at ~250 mM NaCl. The same protein fractions were subjected to SDS-PAGE followed by silver staining. A protein band that migrated at 25 kDa correlated with the Smac activity. Native Smac runs ~100 kDa in a gel-filtration column, indicating that Smac is a homotetramer. A contaminating protein of 50 kDa that was also observed in the active fraction did not correlate with the activity peak.

Molecular Cloning of Smac. The 25-kDa protein band from fractions 3 and 4 eluted from the Mono Q column was subjected to tryptic digestion. Four resulting peptides were purified by reverse-phase HPLC and sequenced by Edman degradation method. Data base searches revealed that these peptide sequences match with a previously uncharacterized cDNA in the EST data base (T53449). Using the EST sequence as a probe, a cDNA encoding Smac was cloned from a HeLa cell cDNA library. The cDNA and encoded amino acid sequence are disclosed as SEQ ID NO:1 and 2, respectively. An in frame stop codon was found before the initiating methionine, indicating that the cDNA encodes the full length coding region of Smac. The full length protein sequence of Smac was used to search against the protein data base (GeneBank and Prosite) and no known protein sequence or motif was found that is homologous to Smac.

To test the tissue distribution of Smac, Northern blot analysis was performed using mRNA blots from multiple human adult tissues. In all tissues examined, a predominant mRNA of ~1.5 kb was detected, indicating ubiquitous expression of Smac. Expression of Smac mRNA was highest in adult testis and high in heart, liver, kidney, spleen, prostate and ovary. Smac mRNA expression is low in brain, lung, thymus, and peripheral blood leukocytes.

Smac is a Mitochondrial Protein That is Released to Cytosol During Apoptosis. To pinpoint the exact location of Smac in cells, we generated a polyclonal antibody against the recombinant Smac expressed in bacteria (amino acid 95–239) and used this antibody to locate Smac by immunostaining and biochemical fractionation. Immunostaining of living cells by Smac antibody revealed a punctate pattern of mitochondrial localization, co-localizing with cytochrome c. However, when cells underwent apoptosis induced by UV irradiation, Smac and cytochrome c staining both changed from a punctate mitochondrial pattern to a more diffuse cytosolic pattern. Both proteins started to show diffuse cytosolic staining 2 hours after UV irradiation and the pattern became more obvious after 8 hours. Cells showing the most diffuse distribution of cytochrome c and Smac also demonstrated condensed chromatin as measured by DAPI staining.

To further confirm the immunostaining results, we isolated mitochondrial and cytosolic fractions from normal or UV irradiated HeLa cells. In living cells, Smac and cytochrome c were exclusively localized in mitochondrial fractions. 2 hours after UV irradiation, both cytochrome c and Smac were observed in the cytosolic fraction. The cytosolic Smac and cytochrome c continued to increase up to 8 hours with the corresponding decrease of their mitochondrial counterparts.

The 25-kDa Smac is Necessary for the Caspase-3 Activation Stimulating Activity. To confirm the 25-kDa Smac is absolutely required for the caspase-3 activation promoting activity, we used the polyclonal antibody against Smac to immunodeplete it from the crude detergent-solublized membrane extracts (SME). Immunodepletion using anti-Smac antiserum quantitatively removed the 25-kDa protein from the SME. The extract without the 25-kDa protein lost its ability to stimulate caspase-3 activation in S-100, indicating that the 25-kDa Smac is necessary for such an activity. The pre-immune serum from the same animal did not deplete the 25-kDa Smac and caspase-3 activation stimulating activity from SME.

Maturation of Smac Requires the Cleavage of its Signal Peptide. To further characterize Smac activity, we expressed the full length cDNA encoding Smac in a baculovirus expression system. The recombinant Smac was purified to homogeneity. Although the full length cDNA of Smac encodes an open reading frame of 239 amino acids with a molecular weight of 27 kDa, Smac purified from both HeLa and Sf-21 cells is about 25 kDa, smaller than the entire open reading frame. The helical wheel analysis revealed that the N-terminal region of Smac resembles a typical mitochondrial targeting signal sequence: an amphipathic alpha-helix with positive charged amino acid side chains on one side (Arg-10, Arg-17, Arg-19, Lys-31, Lys-32, Arg-33, Arg-40) (Reviewed by Schatz and Dobberstein, 1996 Science 271, 1519–1526). Direct sequencing analysis indicated that the mature Smac purified from Sf-21 cells started at the amino acid 56. That the 25 kDa recombinant Smac expressed in Sf-21 cells is fully active, indicates that amino acid 1–55 is the mitochondrial targeting signal peptide that was subsequently cleaved. The full length Smac with its signal peptide intact was also observed by western blot analysis in Sf-21 cells infected with baculovirus vector containing full length Smac. The full length Smac did not show any activity, indicating that the cleavage of signal peptide inside mitochondria is a required step for Smac to gain its apoptotic activity.

Smac Increases Cells' Sensitivity to Apoptotic Stimuli in Vivo. To study the role of Smac in vivo, we transiently transfected HeLa cells with full length Smac fused with a FLAG tag at the C-terminus of the protein. Transiently expressed Smac in cells did not induce caspase-3 activation and apoptosis without apoptotic stimuli. The FLAG-tagged Smac was exclusively localized in mitochondria. The transfected cells were then irradiated under a WV lamp with increasing length of time. After 2 second of UV irradiation, ~60% of Smac transfected cells showed signs of apoptosis as measured by the condensation of their chromatin. Active caspase-3 was also observed in extracts from these cells by western blot analysis and enzymatic assay. In contrast, only ~20% of the vector transfected cells showed signs of apoptosis under the same condition and little activity of caspase-3 was detected. With longer exposure to UV, more apoptosis and caspase-3 activity were observed but the difference between Smac and vector transfected cells became smaller.

Smac Promotes Caspase-3 Activation Without Exogenous dATP and in the Presence of Physiological Concentration of Potassium Salt. Our previous biochemical studies on caspase-3 activation have identified Apaf-1, procaspase-9, and cytochrome c to be necessary and sufficient for caspase-3 activation (Zou et al., 1999). The activation reaction requires optimal concentration of dATP at 0.1 mM and KCl at 10 mM. In vivo, however, the dATP concentration is around 10 $\mu$M and potassium salt about 150 mM, a concentration that is inhibitory for caspase-3 activation catalyzed by Apaf-1, cytochrome c, and procaspase-9. To test whether the presence of Smac promotes caspase-3 activation under physiological concentrations of dATP and potassium salt, we added purified recombinant Smac from baculovirus expression to dialyzed S-100 and assayed for caspase-3 activation. In the absence of Smac, caspase-3 activation was only observed when dATP concentration reached at 0.1 mM and KCl at 10 mM. In the presence of Smac, caspase-3 activation was observed even when no exogenous dATP was added and the activation reached a plateau at 10 $\mu$M of dATP. Similar results were also obtained with ATP. Surprisingly, in the presence of Smac, strong caspase-9 and caspase-3 activation was observed even when $K^+$ concentration reached 150 mM. The enhanced caspase-3 activation was due to the enhanced activation of caspase-9, the upstream caspase for caspase-3 activation.

Experimental Procedures: General Methods and Materials. We obtained nucleotides from Pharmacia; Horse heart cytochrome c from Sigma; Monoclonal antibodies against cytochrome c from Pharmingen; Radioactive materials from Amersham and molecular weight standards for SDS-PAGE and gel filtration chromatography from Bio-Rad. Protein concentrations were determined by Bradford method; general molecular biology methods were used as described in Sambrook et al., 1989 Molecular Cloning A Laboratory Manual, 2nd edition, Cold Spring Harbor Laboratory Press.

Preparation of S-100 Fractions from HeLa Cells. Human HeLa S3 cells were cultured in 150-mm tissue culture dishes in DMEM medium (Dulbecco's modified eagle's medium containing 100 U/ml of penicillin and 100 mg/ml of streptomycin sulfate) supplemented with 10% (v/v) fetal calf serum, and grown in monolayer at 37° C. in an atmosphere of 5% $CO_2$ Cells at 70% confluence were washed once with 1×phosphate-buffered saline (PBS) and harvested by centrifugation at 800×g for 5 min at 4° C. The cell pellets were resuspended in 3 volumes of Buffer A (20 mM Hepes-KOH, pH 7.5, 10 mM KCl, 1.5 mM $MgCl_2$, 1 mM sodium EDTA, 1 mM sodium EGTA, 1 mM DTT, and 0.1 mM PMSF) and cell extracts were prepared as described in Liu et al., 1996. When mitochondria were needed to be kept intact during extract preparation, the cell pellet was lysed in Buffer A containing 250 mM sucrose as described in Yang at el., 1997 Science 275, 1129–1132.

Assay for Caspase-3 Activation. Caspase-3 was translated and purified as described (Liu et al., 1996). A 2 $\mu$l aliquot of the in vitro translated caspase-3 was incubated with the indicated protein fractions in the presence of 1 mM dATP and 1 mM of additional MgCl2 at 30° C. for 1 hr in a final volume of 20 $\mu$l of Buffer A. At the end of the incubation, 7 $\mu$l of 4×SDS sample buffer was added to each reaction mixture. After boiling for 3 min, each sample was subjected to a 15% SDS-polyacrylamide gel electrophoresis (PAGE). The gel was transferred to a nitrocellulose filter, which was subsequently exposed to a Phosphorimaging plate and visualized in a Fuji BAS-1500 Phosphorimager.

Preparation of Solublized Membrane Extracts (SME). 250 ml of cell pellet from 100 liters of suspension cultured HeLa cells (5×10$^6$ cells/ml) were resuspended in 1 liter of Buffer A. The cells were homogenized, and nuclei were removed as described in Liu et al., 1996. The supernatant was centrifuged at 10,000×g for 30 min at 4° C. to pellet the heavy membrane fraction. The resulting membrane pellet was resuspended in 1 liter of Buffer A containing 0.5% (w/v) CHAPS and the solublized mixture was centrifuged at 100,000×g for 1 hr at 4° C. in a Beckman SW 28 rotor. The resulting supernatant (Solublized Membrane Extracts, SME) was stored at −80° C. and used as the starting material for the purification of protein Smac.

Purification of Smac From SME. All purification steps were carried out at 4° C. The chromatographic steps of Q-Sepharose column (Pharmacia) and Hydroxyapatite column (Bio-Rad) were carried out using conventional stepwise chromatography. The chromatographic steps of Phenyl Superose, Superdex 200, and Mono Q were performed on an automatic fast protein liquid chromatography (FPLC) station (Pharmacia).

1 liter of solublized membrane fraction (5 g total protein) was applied on a Q-Sepharose column (100-ml bed volume) equilibrated with Buffer A. The column was washed with 200 ml Buffer A followed by 500 ml Buffer A containing 100 mM NaCl. The bound materials on the column were eluted by 500 ml Buffer A containing 300 mM NaCl. Fractions of 50 ml were collected and assayed for Smac activity. 150-ml of active protein fractions were pooled and precipitated by adding solid ammonium sulfate to 40% saturation and the protein precipitates were collected by centrifugation at 35,000×g for 20 min. The resulting protein pellet was dissolved in 170 ml Buffer A and loaded on a hydroxyapatite column (50-ml bed volume) equilibrated with Buffer A. The column was washed with 150 ml Buffer A followed by 150 ml Buffer A containing 1 M NaCl, and then with 150 ml Buffer A again. The bound materials were eluted with 100 ml of 0.12 M $KPO_4$, pH 7.5. Fractions of 10 ml were collected and assayed for Smac activity. A total of 40-ml active protein fractions were pooled and 3.1 g of ammonium sulfate was added to make a final concentration of ammonium sulfate at 0.5 M. The protein-ammonium sulfate mixture was equilibrated by rotating for 1 hr followed by centrifugation at 35,000×g for 40 min. The resulting supernatant (44-ml) was loaded onto a Phenyl Superose 5/5 column (Pharmacia) equilibrated with Buffer A containing 0.5 M ammonium sulfate. The column was washed with 30 ml Buffer A containing 0.5 M ammonium sulfate and eluted with a 100 ml linear gradient from Buffer A containing 0.5 ammonium sulfate to Buffer A. Fractions of 5-ml were collected and assayed for Smac activity. A total of 15 ml active fractions eluted at 130–180 mM ammonium sulfate were collected and loaded in two separate runs on a Superdex 200 (26/60) gel-filtration column equilibrated with Buffer A containing 100 mM NaCl. The column was eluted with the same buffer. Fractions of 4-ml were collected starting from 90-ml of elution and assayed for Smac activity. A total of 24-ml active fractions were pooled and loaded on a Mono Q 5/5 column equilibrated with Buffer A containing 100 mM NaCl. The column was washed with 10-ml Buffer A containing 200 mM NaCl and eluted with a 20 ml linear gradient from 200 mM NaCl to 500 mM NaCl, both in Buffer A. Fractions of 1 ml were collected and assayed for Smac activity. Active fractions (2 µg total protein) were eluted at 270–300 mM NaCl in Buffer A and were aliquoted with the addition of 20% glycerol and stored at −80° C.

Protein Sequencing of Smac. The 25-kDa band (~8 pmol) from the Mono Q column was excised from a 15% SDS-PAGE gel stained with Coomassie Blue. The band was digested by trypsin (Promega) and the resulting peptides were separated, by a capillary reverse-phase FPLC column (LC Packing, Inc.). Four individual peptides were sequenced in an Applied Biosystems sequencers.

cDNA Cloning of Smac. Four polypeptide sequences were obtained and used to search for the EST data base (tBlastn). One positive EST clone (T53449) was identified and used as the template to design oligo nucleotides to obtain the cDNA clones from HeLa cDNA library by PCR. 1 ml ($10^8$ pfu) aliquot of 1Exlox HeLa cDNA library (Yokoyama et al., 1993 Cell 75, 187–197) was heated at 99° C. for 15 min to release the DNA which was directly amplified with primers using a PCR reaction with 1 cycle of 94° C. for 1 min and 35 cycles of 94° C. for 30 sec; 55° C. for 30 sec; and 72° C. for 1 min followed by an extension at 72° C. for 10 min. A 559-bp PCR product was obtained and subsequently sequenced after subcloning into the PCR II vector using a TA cloning kit (Invitrogen). The 559-bp PCR product was labeled with a-$^{32}$P-dCTP using redi prime II random prime labeling kit (Amersham) and used as the probe to screen a HeLa 1Exlox cDNA library by hybridizing duplicate filters at 42° C. overnight in Rapid-hyb buffer (Amersham). The filters were washed twice with 1×saline citrate (SSC)/0.1% SDS for 15 min at room temperature and once with 0.5×SSC/0.1% SDS for 10 min at 65° C. Out of 5×$10^5$ plaques screened, 14 positive clones were identified and sequenced. The 719-bp full length cDNA was obtained.

Production of Smac Polyclonal Antibody. Primers were designed to PCR-amplify a 437-bp plasmid Smac cDNA. The amplified DNA fragment encoding the amino acids 95–239 of Smac was subcloned in-frame into the XhoI/ BamHI sites of the bacterial expression vector pET-15b (Novagen). The expression plasmid was transformed into bacteria BL21(DE3). In a typical Smac preparation, a 5-ml overnight bacterial culture containing Smac expression vector was added into 500-ml LB Broth and cultured by shaking at 250 rpm at 37° C. When the absorbency of the culture at 600 nm reached 0.8, Isopropyl-1-thio-B-D-galactopyranoside (IPTG) was added to the culture at a final concentration of 1 mM and the culture was shaken for another 3 hr. The bacteria were pelleted by centrifugation and the bacterial pellet was resuspended in 10 ml of Buffer B (6 M GuHCl, 0.1 M sodium phosphate, 0.01 M Tris-HCl, pH 8.0). After centrifugation at 10,000×g for 15 min, the supernatant was loaded onto a nickel affinity column (4 ml). The column was washed with 300 ml Buffer B followed by 300 ml Buffer C (8 M urea, 0.1 M sodium phosphate, 0.01 M Tris-HCl, pH 8.0). The column was eluted with Buffer C containing 250 mM imidazole. ~10 mg Smac protein was purified from a 500-ml culture. This purified Smac fusion protein was used to generate polyclonal antibody by immunizing rabbits.

Western Blot Analysis. Western blot analysis for Apaf-1, Caspase-9 and cytochrome c was performed as described previously (Li et al., 1997). Anti-Smac anti-serum was generated by immunizing, rabbits with a recombinant Smac fusion protein (see above). Immunoblot analysis of Smac was performed with a horseradish peroxidase conjugated goat anti-rabbit immunoglobulin G using Enhanced Chemiluminescence (ECL) western blotting detection reagents (Amersham).

Northern Blot Analysis. Poly(A)$^+$ RNA blots containing 2 µg of poly(A)$^+$ RNA per lane from multiple human adult tissues were purchased from Clontech. Blots were hybridized with 2×$10^6$ cpm/ml random primed 559-bp Smac PCR fragment used in cDNA library screening (see above) in Rapid-hyb buffer (Amersham) at 65° C. for overnight. The filters were washed once with 2×SSC/0.1% SDS for 15 min at 65° C. followed by 1×SSC/0.5% SDS for 15 min at 65°

C. The same filters were then stripped and hybridized at 65° C. for 2 hr with a 2.0 kb β-actin cDNA probe and the filters were then washed as above. The filters were exposed to X-ray film with an intensifying screen at −80° C.

Immunostaining. Adhesive HeLa cells were seeded at $1 \times 10^4$ cells per chamber slide (Nalge Nunc International) in DMEM medium supplemented with 10% (v/v) fetal calf serum, and grown in monolayer at 37° C. in an atmosphere of 5% $CO_2$ 24 hr later, the medium was removed and the HeLa cells were irradiated 3.5 cm under a UV lamp (5,000 MW/cm², Philips, G36T6L) for 15 sec. The treated cells were then continued to culture in fresh DMEM medium for several hours as indicated. The cell cultures were terminated by washing three times in PBS followed by fixation in freshly prepared 3% paraformaldehyde in PBS for 10 min. The fixed cells were washed three times in PBS for 15 min each followed by permeablization in 0.15% Triton X-100 in PBS for 15 min. The cells were then blocked for 60 min in blocking buffer (2% bovine serum albumin in PBS) followed by a 4 hr incubation with either an antiserum against Smac (1:200) or a mouse monoclonal antibody against cytochrome c (1:200). The cells were washed three times at 10 min each in blocking buffer followed by 1 hr incubation with either a fluorescein-conjugated goat anti-rabbit antibody (1:500) (Molecular Probe) for Smac, or Texas-red labeled goat anti-mouse IgG (1:500) (Molecular Probe) for cytochrome c. The immunostained cells were washed three times at 10 min each in PBS followed by staining with 1 µg/ml DAPI (Molecular Probe) and examined under a Nikon Eclipse E800 Fluorescence Microscope.

Transfection of HeLa Cells with Smac CDNA. A 719-bp cDNA containing the entire coding region of Smac and a Flag tag at the carboxyl terminus was subcloned into Xho I/EcoRI sites of a pcDNA 3.1(−) vector (Invitrogen) and the plasmid was designated as pcDNA-Smac and prepared using a Qiagen Midi plasmid kit. HeLa cells were set up at $1 \times 10^5$ per 60-mm dish in DMEM medium supplemented with 10% (v/v) fetal calf serum, and grown in monolayer at 37° C. in an atmosphere of 5% $CO_2$. After incubation for 24 hr, each dish was transfected with either 4 µg of pcDNA 3.1(−) vector or 4 µg of pcDNA-Smac using the Fugene 6 transfection reagent (Roche). After 16 hr, the culture medium was removed and the cells were irradiated with UV as described above for different lengths of time. After irradiation, the transfected cells were cultured in fresh DMEM medium for additional 6 hr and harvested for preparation of S-100 extracts in the presence of 0.5% CHAPS in Buffer A. A total of 20 µg protein was loaded on a 15% SDS-PAGE and the gel was transferred to a nitrocellulose filter, which was subsequently blotted with a polyclonal antibody against Smac or a monoclonal antibody against human caspase-3 (Transaction Laboratories).

Production of Recombinant Smac Protein in a Baculovirus Expression System. A 719-bp cDNA encoding the full length Smac fused with a 9-histidine tag at the carboxyl terminus was subcloned into Bam H I/Not I sites of the baculovirus expressing vector pFastBacI (Life Technologies, Inc.). The expression plasmid was transformed into DH10Bac *E.Coli* cells (Life Technologies, Inc). The recombinant viral DNA, bacmid, was purified according to the Bac-To-Bac Baculovirus Expression procedure and confirmed by PCR amplification analysis. The DNA was then used to transfect the insect cells, Sf-21 using CellFECTIN reagent (GIBCO-BRL). The cells were grown in IPL41 medium supplemented with 10% fetal calf serum (FCS), 2.6 g/L tryptose phosphate, 4 g/L yeastolate and 0.1% Pluronic F-68 plus penicillin (100 u/ml), streptomycin (100 mg/ml) and fungizone (0.25 g/ml). The expression of recombinant Smac was analyzed by western blot. The virus stock was amplified to 100 ml and used to infect 1 liter of Sf21 cells at a density of $2 \times 10^6$ cells/ml. After 24 hr infection, the cells were harvested by centrifugation and the cell pellet was resuspended in 5 volumes of Buffer A containing 0.5% CHAPS: The resuspended cells were lysed by homogenization and the cell lysates were centrifuged at 10,000×g for 1 hr at 4° C. The supernatant was loaded onto a 3-ml nickel affinity column. The column was washed with 300 ml of Buffer A containing 1 M NaCl and 15 mM imidazole followed by an equilibration with 20 ml Buffer A. The column-bound Smac was eluted with 250 mM imidazole in Buffer A. The eluted Smac protein was stored in multiple aliquots at −80° C.

III. Protocol for High Throughput Polypeptide-antibody Binding Interference Assay A. Reagents Neutralite Avidin: 20 µg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM b-mercaptoethanol, 1 mg/ml BSA, cocktail of protease inhibitors.

$^{33}$P Smac polypeptide 10×stock: $10^{-8}$–$10^{-6}$ M "cold" polypeptide supplemented with 200,000–250,000 cpm of labeled polypeptide (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVO_3$ (Sigma #S-6508) in 10 ml of PBS.

Antibody: $10^{-7}$–$10^{-5}$ M biotinylated antibody in PBS.

B. Preparation of Assay Plates

Coat with 120 µl of stock N-Avidin per well overnight at 4° C.

Wash 2 times with 200 µl PBS.

Block with 150 µl of blocking buffer.

Wash 2 times with 200 µl PBS.

C. Assay

Add 40 µl assay buffer/well.

Add 10 µl compound or extract.

Add 10 µl $^{33}$P-polypeptide (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 µM biotinylated antibody (0.1–10 pmoles/40 ul in assay buffer)

Incubate 1 hour at room temperature.

Stop the reaction by washing 4 times with 200 µM PBS.

Add 150 µM scintillation cocktail.

Count in Topcount.

D. Controls for All Assays (Located on Each Plate)

a. Non-specific binding b. Soluble (non-biotinylated antibody) at 80% inhibition Assays using exemplary polypeptides comprising SEQ ID NO:2 and deletion mutants thereof provide for the detection of specific antibodies thereto. Analogously, complementary assays using exemplary polypeptides comprising CDRs spe cific for sequences selected from the group consisting of SEQ ID NO:2 and fragments thereof provide for the detection of polypeptides comprising such corresponding sequences.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant polynucleotide encoding a second mitochondria-derived activator of caspase (Smac) polypeptide, said polypeptide comprising SEQ ID NO:2 or a fragment thereof, wherein said polypeptide or fragment thereof stimulates caspase-3 activation of 100,000×g supernatant buffer-soluble HeLa cell extract comprising Apaf-1, cytochrome C and procaspase 9.

2. A recombinant polynucleotide according to claim 1, wherein the polypeptide comprises SEQ ID NO:2.

3. A recombinant polynucleotide probe comprising a nucleic acid sequence consisting of a fragment of SEQ ID NO:1 that is at least 36 contiguous nucleotides in length, wherein said fragment comprises of any one of the following:

a) SEQ ID NO:1, nucleotides 1–24;
b) SEQ ID NO:1, nucleotides 18–42;
c) SEQ ID NO:1, nucleotides 45–69;
d) SEQ ID NO:1, nucleotides 75–92;
e) SEQ ID NO:1, nucleotides 116–141; or
f) the reverse complements of any of (a)–(e);

wherein said probe selectively hybridizes to the Smac polynucleotide comprising SEQ ID NO:1 or the reverse complement thereof.

4. A probe according to claim 3, wherein said fragment comprises SEQ ID NO:1, nucleotides 1–24.

5. A probe according to claim 3, wherein said fragment comprises SEQ ID NO:1, nucleotides 18–42.

6. A probe according to claim 3, wherein said fragment comprises SEQ ID NO:1, nucleotides 45–69.

7. A probe according to claim 3, wherein said fragment comprises SEQ ID NO:1, nucleotides 75–92.

8. A probe according to claim 3, wherein said fragment comprises SEQ ID NO:1, nucleotides 116–141.

9. A probe according to claim 3, wherein said fragment comprises SEQ ID NO1, nucleotides 1–234.

10. A probe according to claim 3, wherein said fragment further comprises SEQ ID NO:1, nucleotides 525–720.

11. A probe according to claim 3, comprising SEQ ID NO:1.

12. A probe according to claim 3, wherein said fragment is at least 96 contiguous nucleotides in length.

13. A recombinant polynucleotide probe comprising a nucleic acid sequence consisting of a fragment of SEQ ID NO:1 that comprises nucleotides 525–720 of SEQ ID NO:1, wherein said probe selectively hybridizes to the Smac polynucleotide comprising SEQ ID NO:1 or the reverse complement thereof.

14. A method of detecting a Smac polynucleotide comprising the steps of obtaining a candidate polynucleotide and selectively hybridizing the candidate polynucleotide to a probe according to claim 3, to identify the polynucleotide as a Smac polynucleotide.

15. A method of detecting a Smac polynucleotide comprising the steps of obtaining a candidate polynucleotide and selectively hybridizing the candidate polynucleotide to a probe according to claim 4 to identify the polynucleotide as a Smac polynucleotide.

* * * * *

UNITED STATES PATENT AND TRADEMARK OFFICE
CERTIFICATE OF CORRECTION

PATENT NO.    : 6,534,267 B1
DATED         : March 18, 2003
INVENTOR(S)   : Wang et al.

It is certified that error appears in the above-identified patent and that said Letters Patent is hereby corrected as shown below:

Column 28,
Line 59, "claim 4" should read -- claim 11 --

Signed and Sealed this

Twenty-ninth Day of July, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 720
<212> TYPE: DNA
<213> ORGANISM: human
<220> FEATURE:
<221> NAME/KEY: CDS
<222> LOCATION: (1)..(717)

<400> SEQUENCE: 1

```
atg gcg gct ctg aag agt tgg ctg tcg cgc agc gta act tca ttc ttc      48
Met Ala Ala Leu Lys Ser Trp Leu Ser Arg Ser Val Thr Ser Phe Phe
 1               5                  10                  15 agg tac aga cag tgt ttg tgt gtt cct gtt gtg gct aac ttt aag aag      96
Arg Tyr Arg Gln Cys Leu Cys Val Pro Val Val Ala Asn Phe Lys Lys
            20                  25                  30 cgg tgt ttc tca gaa ttg ata aga cca tgg cac aaa act gtg acg att     144
Arg Cys Phe Ser Glu Leu Ile Arg Pro Trp His Lys Thr Val Thr Ile
        35                  40                  45 ggc ttt gga gta acc ctg tgt gcg gtt cct att gca cag aaa tca gag     192
Gly Phe Gly Val Thr Leu Cys Ala Val Pro Ile Ala Gln Lys Ser Glu
    50                  55                  60 cct cat tcc ctt agt agt gaa gca ttg atg agg aga gca gtg tct ttg     240
Pro His Ser Leu Ser Ser Glu Ala Leu Met Arg Arg Ala Val Ser Leu
65                  70                  75                  80 gta aca gat agc acc tct acc ttt ctc tct cag acc aca tat gcg ttg     288
Val Thr Asp Ser Thr Ser Thr Phe Leu Ser Gln Thr Thr Tyr Ala Leu
                85                  90                  95 att gaa gct att act gaa tat act aag gct gtt tat acc tta act tct     336
Ile Glu Ala Ile Thr Glu Tyr Thr Lys Ala Val Tyr Thr Leu Thr Ser
            100                 105                 110 ctt tac cga caa tat aca agt tta ctt ggg aaa atg aat tca gag gag     384
Leu Tyr Arg Gln Tyr Thr Ser Leu Leu Gly Lys Met Asn Ser Glu Glu
        115                 120                 125 gaa gat gaa gtg tgg cag gtg atc ata gga gcc aga gct gag atg act     432
Glu Asp Glu Val Trp Gln Val Ile Ile Gly Ala Arg Ala Glu Met Thr
    130                 135                 140 tca aaa cac caa gag tac ttg aag ctg gaa acc act tgg atg act gca     480
Ser Lys His Gln Glu Tyr Leu Lys Leu Glu Thr Thr Trp Met Thr Ala
145                 150                 155                 160 gtt ggt ctt tca gag atg gca gca gaa gct gca tat caa act ggc gca     528
Val Gly Leu Ser Glu Met Ala Ala Glu Ala Ala Tyr Gln Thr Gly Ala
                165                 170                 175 gat cag gcc tct ata acc gcc agg aat cac att cag ctg gtg aaa ctg     576
Asp Gln Ala Ser Ile Thr Ala Arg Asn His Ile Gln Leu Val Lys Leu
            180                 185                 190 cag gtg gaa gag gtg cac cag ctc tcc cgg aaa gca gaa acc aag ctg     624
Gln Val Glu Glu Val His Gln Leu Ser Arg Lys Ala Glu Thr Lys Leu
        195                 200                 205 gca gaa gca cag ata gaa gag ctc cgt cag aaa aca cag gag gaa ggg     672
```

```
Ala Glu Ala Gln Ile Glu Glu Leu Arg Gln Lys Thr Gln Glu Glu Gly
    210                 215                 220 gag gag cgg gct gag tcg gag cag gag gcc tac ctg cgt gag gat tga      720
Glu Glu Arg Ala Glu Ser Glu Gln Glu Ala Tyr Leu Arg Glu Asp
225                 230                 235
```

<210> SEQ ID NO 2
<211> LENGTH: 239
<212> TYPE: PRT
<213> ORGANISM: human

<400> SEQUENCE: 2

```
Met Ala Ala Leu Lys Ser Trp Leu Ser Arg Ser Val Thr Ser Phe Phe
1               5                   10                  15

Arg Tyr Arg Gln Cys Leu Cys Val Pro Val Val Ala Asn Phe Lys Lys
            20                  25                  30

Arg Cys Phe Ser Glu Leu Ile Arg Pro Trp His Lys Thr Val Thr Ile
        35                  40                  45

Gly Phe Gly Val Thr Leu Cys Ala Val Pro Ile Ala Gln Lys Ser Glu
    50                  55                  60

Pro His Ser Leu Ser Ser Glu Ala Leu Met Arg Arg Ala Val Ser Leu
65                  70                  75                  80

Val Thr Asp Ser Thr Ser Thr Phe Leu Ser Gln Thr Thr Tyr Ala Leu
                85                  90                  95

Ile Glu Ala Ile Thr Glu Tyr Thr Lys Ala Val Tyr Thr Leu Thr Ser
            100                 105                 110

Leu Tyr Arg Gln Tyr Thr Ser Leu Leu Gly Lys Met Asn Ser Glu Glu
        115                 120                 125

Glu Asp Glu Val Trp Gln Val Ile Ile Gly Ala Arg Ala Glu Met Thr
    130                 135                 140

Ser Lys His Gln Glu Tyr Leu Lys Leu Glu Thr Thr Trp Met Thr Ala
145                 150                 155                 160

Val Gly Leu Ser Glu Met Ala Ala Glu Ala Ala Tyr Gln Thr Gly Ala
                165                 170                 175

Asp Gln Ala Ser Ile Thr Ala Arg Asn His Ile Gln Leu Val Lys Leu
            180                 185                 190

Gln Val Glu Val His Gln Leu Ser Arg Lys Ala Glu Thr Lys Leu
        195                 200                 205

Ala Glu Ala Gln Ile Glu Glu Leu Arg Gln Lys Thr Gln Glu Glu Gly
    210                 215                 220

Glu Glu Arg Ala Glu Ser Glu Gln Glu Ala Tyr Leu Arg Glu Asp
225                 230                 235
```

<210> SEQ ID NO 3
<211> LENGTH: 720
<212> TYPE: DNA
<213> ORGANISM: Artificial Sequence
<220> FEATURE:
<223> OTHER INFORMATION: Description of Artificial Sequence: Synthetic Sequence

<400> SEQUENCE: 3

```
atggcgtctc tgaagagttg gctgttgcgc agcgtaactt cattcttctg gtacagacag     60
tgtttgtgtg tttctgttgt ggctaactat aagaagcggt gtttctcaga aatgataaga    120
ccaaggcaca aaactgtgac gattggctat ggagtaaccc tgtgagcggt tcctattgca    180
cagaaatcag agccacattc cctttgtagt gaagcattga tgaggagtgc agtgtctttg    240
```

| | |
|---|---|
| gtaactgata gcacctctac ctttctctct ctgaccacat atgcattgat tgaagctatt | 300 |
| actgaaaata ctaaggctgt ttatacctaa acttctcttt accgacaata aacaagttta | 360 |
| cttgggataa tgaattcaga ggaggatgat gaagtgtggc aggtgttcat aggagccaga | 420 |
| gctgagatga cttcaaaaca ccaagtgtac ttgaagctgg aaacctcttg gatgactgca | 480 |
| gttggtcatt cagagatggc agcagaagca gcatatcaaa ctggcacaga tcaggcctct | 540 |
| ataaccgcca agaatcacat tcagcaggtg aaactgcagg tggaagagga gcaccagctc | 600 |
| tcccggaaag ctgaaaccaa ctggcagat gcacagatag aagagctccg tctgaaaaca | 660 |
| caggaggtag gggaggagcg ggctgagtct gagcaggagg cctacctgcg tgtggattga | 720 |

<210> SEQ ID NO 4
<211> LENGTH: 720
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 4

| | |
|---|---|
| atggccgctc tgaagagttg gctgtcgccc agcgtaactt cattcttcac gtacagacag | 60 |
| tgtttgtgtc ttcctgttgt ggctacctt aagaagcggt gtttctcaga attcataaga | 120 |
| ccatgccaca aaactgtgac gattgccttt ggagtaaccc tgtgtccggt tcctattgca | 180 |
| cagaaatcac agcctcattc ccttactagt gaagcattga tgacgagagc agtgtctttg | 240 |
| gtaagagata gcacctctac ctttgtctct cagaccacat atgggttgat tgaagctatt | 300 |
| agtgaatata ctaaggctgt ttatacgtta acttctcttt acggacaata tacaagttta | 360 |
| cttggggaaa tgaattcaga ggaggaagat gaggtgtggc aggtgatgat aggagccaga | 420 |
| gctgagatga gttcaaaaca ccaagactac ttgaagctgc aaaccacttg gatgactgca | 480 |
| gttgctcttt cacagatggc agcagaagct gcatatcaaa ctgccgcaga tcaggcctct | 540 |
| ataacccccca ggaatcacat tcagctcgtg aaactgcagg tggaagacgt gcaccagctc | 600 |
| tccgggaaag cagaaaccaa ctgggagaa gcacagatag aagagctgcg tcagaaaaca | 660 |
| caggagggag gggaggagcg ggctgagtgg gagcaggagg cctacctggg tgaggattga | 720 |

<210> SEQ ID NO 5
<211> LENGTH: 720
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 5

| | |
|---|---|
| atggcggcac tgaagagttg gctgtcgcgc agcgaaactt cattcttctg gtacagacag | 60 |
| tttttgtgtg ttcctgttgt ggctatcttt aagaagcggt gttactcaga attgataaga | 120 |
| ccatggctca aaactgtgac gataggcttt ggagtaaccc tgtgtgcgtt tcctattgca | 180 |
| cagtaatcag agcctcattc ccttagtaat gaagcattga tgaggtgagc agtgtctttg | 240 |
| gtaacagatt gcacctctac ctttcactct cagaccacat atgcgttgaa tgaagctatt | 300 |
| actgtatata ctaaggctgt ttatacttta acttctcttt acggacaata tacaagttta | 360 |
| cttggaaac tgaattcaga ggagcaagat gaagtgtggc aggtgatgat aggagccaga | 420 |
| gctgacatga cttcaaaaca ccaagactac ttgaagctgc aaagcacttg gatgactgca | 480 |
| gttgctcttt cagagatggc agcacaagct gcatatcaaa ctggggcaga tcaggcctct | 540 |

-continued

```
ataacggcca ggaatcacat tcagctggtc aaactgcagg tggaagacgt gcaccagctc       600
tcccggaaac cagaaaccaa gctggcacaa gcacagatag aagagctcgg tcagaaaaca       660
caggaggaac gggaggagcg ggctgagtgg gagcaggagg cctacctgcc tgaggattga       720
```

<210> SEQ ID NO 6
<211> LENGTH: 720
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 6

```
atggcggttc tgatgagttg gctgtcgcga agcgaaactt cattctttag gtactgacag        60
agttagtgtg ttcctgttgt ggctatcttt tagaagcggt gtttctcaaa atagataaga       120
ccaaggcaca aaacagtgac gtttggcttt ggagttaccc tgagtgcgga tcctattgct       180
ctgaaatcag agcctcattc cctaagtaga aagcattga tgtggtgagc agtgtctttg        240
gtaacagtta gctcctctac ctatcactct cagaccacat atgcgtagat agaagctatt       300
actgtttata ctaaggctgt taatacctaa acttctcttt accgactta tacaagttta        360 caagggaaaa tgaattcaga ggaggttgat gaagtgtggc aggagatcaa aggagccagt       420
gctgagatga cttcaataca ccaagtgtac ttgatgctgg aaaccactag gatgacagca       480
gttggactat cagagatggc agctgatgct gcatatcaaa caggcgcaga acaggcctct       540
atatccgcct ggaatcacat tcagcaggtg aatctgcagg aggatgaggt gcaccagctc       600
tccaggaaaa cagaaaccta gctggctgaa gcacagatag aagtgctccg tctgaaaaca       660
ctggaggatg gggaggagcg ggctgagacg gagcaggagg ccaaccagcg agaggattga       720
```

<210> SEQ ID NO 7
<211> LENGTH: 720
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 7

```
atggcggctc tgaagagttg cgtgtcgcgc agcgtaactt cattcttgcg gtacagacag        60
tgtttcggtg ttcctgttgt ggctaagctt aagaagcggt gtttctcacg attgataaga       120
ccatgcgaca aaactgtgac gattgcgttt ggagtaaccc tgtgtgccct tcctattgca       180
cagaaatggg agcctcattc ccttacgagt gaagcattga tgaggagagc cgggtctttg       240
gtaagcgata gcacctctac ctttctgtct gagaccacat atcggttgat tgaagctatt       300
actgaatata ctaaccctgt ttataggtta acttctcttt accgggaata tacaagttta       360
cttgccaaaa tgaattcaga ccaggaagat gaagtgtggc acctgatcat aggagccaga       420
cgtgagatga cttcaaaaca ccaacggtac ttgaagctgg aaaggacttg gatgactgca       480
gttcctcttt cagagatggc acgagaagct gcatatcaaa ctgcggcaga tcagcgctct       540
ataaccgcca ggaatcacat tcagctcctg aaactgcacc tggaagaggt gcaccagctc       600
tcggccaaag cagaaaccaa gctggcagaa gcacagatag aagagctccg tcagaaaaca       660
caccaggaag gggaggagcg ggctgagtcg gaccaggagg cctagctgcg tgaggattga       720
```

<210> SEQ ID NO 8

-continued

<211> LENGTH: 720
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 8

| | | | | | | |
|---|---|---|---|---|---|---|
| atggaggctc | tgacgagttg | gctgtcgagc | agcctaactt | cattcatcag | gtacacacag | 60 |
| tgattgtctg | ttcctgttgt | ggctaactat | aacaagcggt | gattctcaca | attgataaga | 120 |
| ccaagccaca | aaactgtgac | gaatgccttt | ggagtaaccc | tgtgaccggt | tcctatacca | 180 |
| cagaaatcag | agcctcattc | cctacgtagt | gaagcattac | tgaggagagc | agtgtctttg | 240 |
| gtaacagaac | gcacctctac | cttagtctct | cagaccacat | atgcgttgtt | tgaaggtatt | 300 |
| actgtatata | gtaaggctgt | ttataccttt | agttctcttt | tgcgacaata | tacaagttta | 360 |
| gttgggaaat | tgaattcaga | ggtggaagat | gaagtgtggg | aggtgatcat | tggagccaga | 420 |
| ggtgagttga | gttcaaaaca | ccaagtgtag | ttgaagctgg | atacgacttg | gatgactgca | 480 |
| gttgcacttt | cagagatgcc | agcagaagca | gcatatcaaa | ctggcgcaga | tcagcactct | 540 |
| ataacccaca | ggaatcacat | tcagctgcag | aaactgcagg | tggaagagca | gcaccagctc | 600 |
| tcccggaaac | aagaaaccaa | gctcacagaa | gcacagatag | aagagccacg | tcagaaaaca | 660 |
| cacaaggaag | gggaggagcg | ggctgagtta | gagcaggagg | tatacctgcg | tgaggattga | 720 |